United States Patent [19]
Suzuki et al.

[11] Patent Number: 4,746,532
[45] Date of Patent: May 24, 1988

[54] METHOD FOR THE PRODUCTION OF ENDOSSEOUS IMPLANTS

[75] Inventors: Kazuo Suzuki; Mitsuo Ito, both of Shiojiri, Japan

[73] Assignee: Sumitomo Chemical Company, Limited, Osaka, Japan

[21] Appl. No.: 890,287

[22] Filed: Jul. 29, 1986

[30] Foreign Application Priority Data

Aug. 8, 1985 [JP] Japan ................... 60-175569

[51] Int. Cl.⁴ ............................................. B05D 1/08
[52] U.S. Cl. .................................. 427/2; 427/34; 427/423
[58] Field of Search ............ 427/2, 34, 330, 423; 623/11; 433/173, 174, 175, 176, 201.1

[56] References Cited

U.S. PATENT DOCUMENTS

| | | | |
|---|---|---|---|
| 3,643,658 | 2/1972 | Steinemenan . | |
| 4,145,764 | 3/1979 | Suzuki et al. | 433/176 |
| 4,146,936 | 4/1979 | Aoyagi et al. . | |
| 4,149,910 | 4/1979 | Popplewell | 427/330 |
| 4,159,358 | 6/1979 | Hench et al. | 427/330 |

Primary Examiner—John H. Newsome
Attorney, Agent, or Firm—Birch, Stewart, Kolasch & Birch

[57] ABSTRACT

An improved method for producing endosseous implants by thermally spraying a ceramic material onto the surface of a metallic titanium core material which is previously subjected to a surface oxidation treatment, which can yield implants which have excellent characteristics of both of the metallic material and ceramic material and do not dissolve out harmful metal ions. The endosseous implants are useful for implantation in various bones including tooth roots and joints in living bodies.

9 Claims, 2 Drawing Sheets

Figure 1
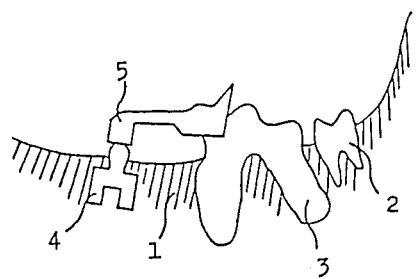
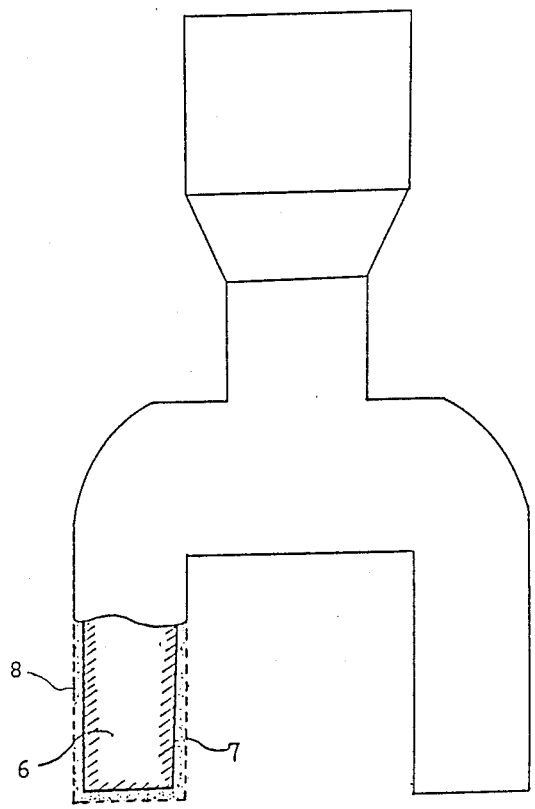
FIG. 2A
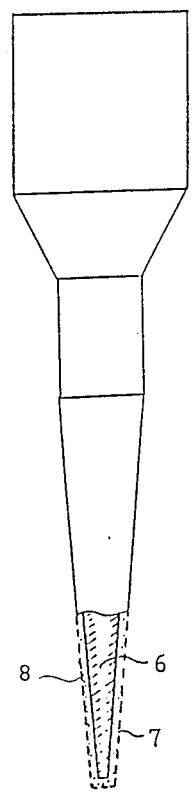
FIG. 2B

The ceramic materials used in this invention include hydroxyapatite, calcium phosphate, aluminum oxide, zirconium oxide, titanium oxide, and the like, which may be used alone or in combination of two or more thereof. In order to control the pores in the ceramic layer, porcelain may be applied by thermally spraying together with the ceramic material or by baking on the ceramic coating layer. For such a purpose, there can be used porcelains such as Dentin and Enamel. Among the ceramic materials, preferred ones are hydroxyapatite and aluminum oxide in view of their excellent affinity with living bodies. A combination of hydroxyapatite and aluminum oxide is particularly suitable because it is most intimate with living bodies.

The endosseous implants of this invention can be produced in the following manner.

The metallic material is formed into the desired shape by conventional methods, such as cutting, casting, forging, punching, electro arc machining, laser-processing, and powdered metal techniques. The surface of the metallic titanium core materials thus formed may be made rough, for example, by mechanical methods such as grinding, sandblasting, grit blasting, etc.; chemical etching such as treatment with an acid or alkali; electrolytic etching; and the like, prior to subjecting to the surface oxidation treatment.

The surface oxidation treatment of the metallic titanium core material can be carried out by various methods, for example, by heat-treatment in air, an anodizing process, and the like, but preferably by heat-treatment in air. The heat-treatment is preferably done at a temperature of 400° to 800° C. When the temperature is lower than 400° C., the ceramic coating layer formed by the thermal spray shows inferior adhesion. On the other hand, when the temperature is higher than 800° C., the strength of the materials is deteriorated and further the surface oxide becomes too thick which causes a lowering of the adhesion of the coating layer. Preferred heating temperature is in the range of 450° to 550° C. in view of the excellent adhesion of the coating layer and the strength of the materials. The heat-treating period of time is not specified, but is preferably in the range of 1 to 100 minutes in the practical viewpoint. The heat-treatment of the metallic titanium core material is usually carried out in a conventonal electric furnace or gas furnace.

In the thermal spraying of ceramic materials, the portion which is not coated with the ceramic material is previously masked by an appropriate means, for instance, application of a marking ink, an aluminum adhesive tape, etc., prior to the treatment for making the surface rough. The thermal spraying of the ceramic material is also preferably carried out by a thermal plasma spraying apparatus. Some portions of the endosseous implants, for instance, the ceramic coating layer in artificial joints, are required to have high smoothness. In such a case, a porcelain is coated onto the surface and the coated product is repeatedly calcined in a vacuum furnace.

In the endosseous implants of this invention, the thickness of the ceramic coating layer which optionally contains the porcelain is not particularly limited, but is preferably in the range of 10 to 200 μm.

This invention is illustrated by the following Examples but should not be construed to be limited thereto.

EXAMPLE

A core material for an endosseous implant is prepared by using a titanium material (JIS, second class of material) in the following manner, i.e. by cutting and grinding the titanium material by electro arc machining.

The metallic core material for implant is gritblasted with a blast apparatus (a mammoth type ventiblast apparatus, manufactured by Metco Inc., England; blasting agent: Metcolite VF, manufactured by Metco Inc.; pressure: 30 psi).

The plasted core material is heat-treated at 500° C. for 10 minutes. Thereafter, under generation of argon-hydrogen-plasma jet flame (ARC electric current 500 Amp) by a plasma spray apparatus (6MM-630 type, manufactured by Metco Inc., equipped with an electric power supplier), a ground mixture of hydroxyapatite (particle size: 10–100 μm, 80% by weight) and aluminum oxide (WA #120, manufactured by Nippon Kenmazai K.K., 20% by weight) is thermally sprayed to form a coating layer having an average thickness of about 150 μm. The thermally sprayed coating layer has excellent adhesion, and even when the product is subjected to a bending process at an angle of 160°, the coating layer is not peeled off.

The product obtained above was tested as follows:

The implant was embedded into the lower jawbone of dog. After 3 months, it was observed by X-ray fluoroscopy. As a result, there was confirmed the formation of dense bone around the implant.

The correlations of the temperature in the heat-treatment with the adhesion of the coating layer and also with the elastic modulus of the core material are shown in the accompanying FIG. 3 and FIG. 4, respectively, wherein the data in the Reference Example are also shown. The sample (width 5 mm × thickness 1 mm × length 50 mm) used in the test was prepared from the same material as used in the Example in the same manner. The adhesion of the coating layer and the elastic modulus of the core material were measured by a three-point bending test where the sample was kept at a span distance of 30 mm. As is clear from FIG. 3 and FIG. 4, the temperature for the heat-treatment is preferably in the range of 400° to 800° C.

REFERENCE EXAMPLE

A core material for an endosseous implant is prepared by using the same titanium material in the same manner as described in Example. The core material is subjected to grid blasting likewise, but is not subjected to heat-treatment.

The blasted core material is thermally sprayed with a powdery mixture of titanium oxide and aluminum oxide in a layer having an average of about 50 μm as the first coating layer, and then further thermally sprayed thereon with a mixture of hydroxyapatite and aluminum oxide in a layer having an average of about 150 μm as the second coating layer. The resulting product has significantly inferior adhesion of the coating layer and the coating layer is easily peeled off even by a light impact. This product cannot be used as an endosseous implant.

Thus, according to the present invention, by thermally spraying a ceramic material on the surrounding suface of a metallic titanium core material which is surface-oxidized, there can be produced excellent endosseous implants which improve the defect of ceramic implants being easily breakable while keeping excellent

METHOD FOR THE PRODUCTION OF ENDOSSEOUS IMPLANTS

The present invention relates to a method for the production of endosseous implants, and more particularly to an improved method for the production of endosseous implants which do not dissolve out metal ions.

BACKGROUND OF THE INVENTION

The implantology which comprises the insertion of artificial materials such as artificial organs, artificial blood vessels, artificial joints, artificial bones and artificial tooth roots into living bodies so as to recover lost parts of living bodies or their functions has received much attention in recent years. It is said that a trial of implantation goes back to ancient times. Particularly in these ten-odd years, a huge number of treatments by implantation have been performed on bones and tooth roots to afford good results in the remedy of the defects or recovery of functions thereof. However, there has not yet been obtained an artical bone or tooth root which satisfies the necessary requirements as material for living bodies, i.e. affinity to living bodies, safety, and excellent durability.

As metallic materials which have mainly been used for preparation of artificial bones or tooth roots, cobalt-chromium alloys, stainless steel, titanium and tantalum are exemplified. On the other hand, as ceramic materials, alumina or materials comprising predominantly carbon have been recently taken note of.

Although metallic materials have excellent mechanical strength, particularly impact strength, they are deficient in their affinity to tissues of living bodies. For example, when a metallic implant is used, metal ions are dissolved out therefrom in living bodies and affect a toxic action to bone cells around the implant. Furthermore, the bone-formation is obstructed probably because the thermal conductivity of the metallic implant is too high. Among the metallic materials, titanium and tantalum are particularly superior in a corrosion-resistance and hence have been employed as fixing plates for skulls or fractured parts of bones and implants for jawbones since about 1940, but these are not necessarily satisfactory.

To the contrary, ceramic materials show generally a good affinity to bones, and hence tissues penetrate into fine pores of the ceramic materials to afford a strong fixation, without reaction between the ceramic material and the tissue. Besides, they are also excellent in durability, that is, they are resistant to corrosion decomposition. On the other hand, they posses poor impact strength.

There has been proposed an implant having the characteristics of both of metallic materials and ceramic materials, i.e. an implant prepared by thermally spraying a ceramic material onto the surface of a metallic core material (cf. Japanese Patent First Publication Nos. 14095/1977, 82893/1977, 28997/1978 and 75209/1978). In these methods, however, a self-bonding type bonding agent is used in order to improve the adhesion of the ceramic coating layer. The bonding agent has a problem in that it contains nickel, chromium, etc. which dissolve out in living bodies and exhibit toxicity to living bodies.

SUMMARY OF THE INVENTION

The present inventors have intensive conductive studies develop improved endosseous implants which have excellent impact strength and hence resistance to cracking while keeping the excellent properties of ceramic materials and further do not dissolve out toxic metal ions, and have now found that the desired endosseous implants can be prepared by thermally spraying a ceramic material onto a metallic titanium core material which is previously subjected to surface oxidation.

An object of this invention is to provide an improved endosseous implant which has excellent characteristics of both of a metallic material and a ceramic material and does not dissolve out toxic metal ions.

Another object of the invention is to provide an improved method for producing the excellent endosseous implant by thermally spraying a ceramic material onto a metallic titanium core material which is previously subjected to a surface oxidation treatment.

A further object of the invention is to provide a method for producing the excellent endosseous implant without using any bonding agent which contains toxic metal ions.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 1 is a schematic view of an embodiment of the endosseous implant for a lower jawbone of dog, wherein 1 represents the lower jawbone, 2 and 3 are natural teeth, 4 is an artificial tooth root and 5 is an artificial tooth crown attached on the artificial tooth root 4.

FIG. 2 is a partially lacked schematic view of an embodiment of the endosseous implant for a jawbone of a blade type according this invention, and (A) is a front view thereof and (B) is a side view thereof, wherein 6 represents a surface-oxidized metallic titanium core material and 7 and 8 are each a thermally plasma sprayed layer comprising predominantly ceramics.

DETAILED DESCRIPTION OF THE INVENTION

Figure 3:
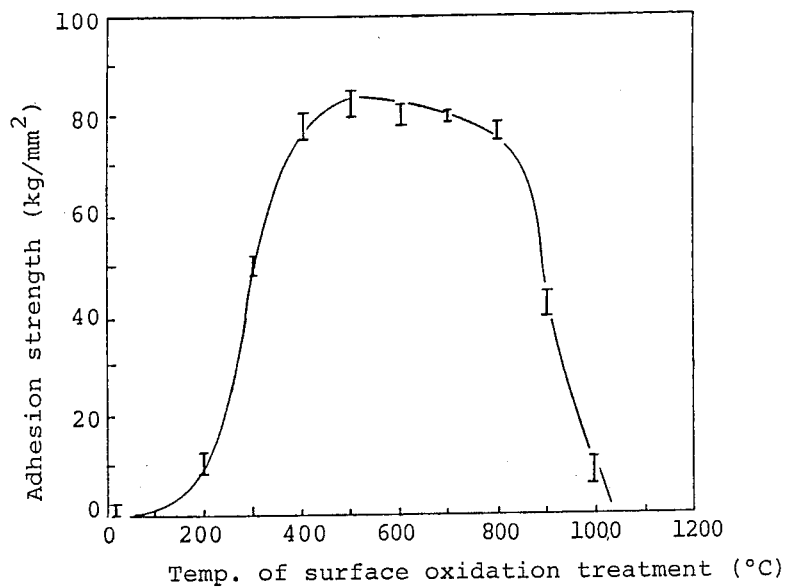
FIG. 3 is a graph showing a correlation between a heating temperature of titanium material and an adhesion strength of the coating layer formed by the thermal plasma spray.
Figure 4:
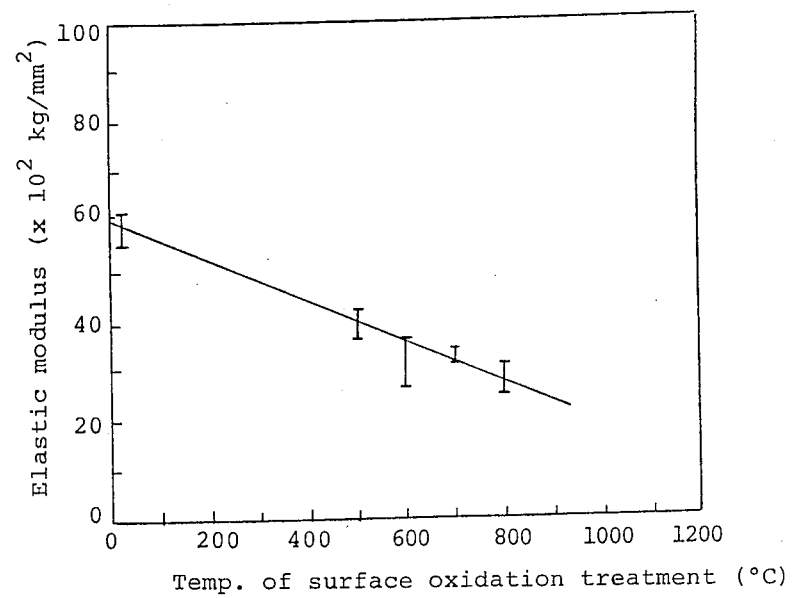
FIG. 4 is a graph showing a correlation between a heating temperature of titanium material and a change of the elastic modulus of the titanium material.

According to the present invention, as is shown in FIG. 2, a ceramic coating is applied to the surface of a metallic implant core material so as to obtain an implant being hardly breakable with a sufficient impact strength and acting to the surrounding bone tissues in a similar manner as ceramic materials.

The metallic core materials used in this invention include any conventional titanium materials which have usually been used as artificial materials for bones, joints and tooth roots which do not exhibit harmful influences on living bodies and possess an appropriate mechanical strength, for example, titanium and titanium alloys (e.g. 6% Al-4% V-Ti, etc.).

characteristics of the ceramic material. The present implants have excellent mechanical strength of metallic material and further can act to the surrounding bone tissues in a similar manner as ceramic material.

What is claimed is:

1. In a method for producing endosseous implants comprising thermally spraying a ceramic material onto the surface of a metallic titanium core material, the improvement which comprises subjecting the metallic titanium core material to a surface oxidation treatment by heating the core material at a temperature of 400° to 800° C. in air and then thermally spraying the ceramic material onto the surface of the metallic titanium core material, wherein the ceramic material is aluminum oxide, hydroxyapatite or a mixture thereof.

2. The method according to claim 1, wherein the temperature for the surface oxidation treatment is in the range of 450° to 550° C.

3. The method according to claim 1, wherein the surface of the metallic titanium core material is made rough prior to subjecting to the surface oxidation treatment.

4. An endosseous implant which is produced by the method as set forth in claim 1.

5. The method according to claim 1, wherein the thermal spraying is carried out by thermal plasma spraying.

6. The method according to claim 1, wherein the surface oxidation treatment is conducted for 1 to 100 minutes.

7. The method according to claim 1, wherein the thickness of the ceramic coating layer is from 10 to 200 μm.

8. The implant according to claim 4, wherein the thickness of the ceramic coating layer is from 10 to 200 μm.

9. The method according to claim 1, wherein a ground mixture of hydroxyapatite and aluminum oxide is thermally sprayed to form a coating layer having an average thickness of about 150 μm.

* * * * *